United States Patent [19]

Zhang

[11] Patent Number: 5,929,164
[45] Date of Patent: Jul. 27, 1999

[54] QUENCHING POST CURE

[75] Inventor: Shizhong Zhang, Midland, Mich.

[73] Assignee: Dow Corning Corporation, Midland, Mich.

[21] Appl. No.: 08/964,546

[22] Filed: Nov. 5, 1997

[51] Int. Cl.$^6$ ........................................... C08L 83/05
[52] U.S. Cl. .................. 524/862; 524/731; 524/924; 525/479; 525/478; 528/15; 528/502 F; 424/401
[58] Field of Search ..................... 524/862, 731, 524/924; 424/401; 528/15, 502; 525/479, 478

[56] References Cited

U.S. PATENT DOCUMENTS

| | | | |
|---|---|---|---|
| 4,851,166 | 7/1989 | Kendall | 264/22 |
| 4,961,963 | 10/1990 | Peters | 427/208.8 |
| 5,004,792 | 4/1991 | Maxson | 528/15 |
| 5,548,006 | 8/1996 | Hirabayashi et al. | 524/82 |
| 5,623,030 | 4/1997 | Tsumura et al. | 525/478 |
| 5,654,362 | 8/1997 | Schulz | 524/862 |

*Primary Examiner*—Robert Dawson
*Assistant Examiner*—Caixia Lu-Rutt
*Attorney, Agent, or Firm*—James L. De Cesare

[57] ABSTRACT

A method of thickening solvents involves reacting (A) an $\equiv$Si—H containing polysiloxane with (B) an alpha, omega-diene; conducting the reaction in the presence of a platinum catalyst and (C) a solvent; continuing the reaction until a gel is formed by crosslinking and addition of $\equiv$Si—H across double bonds in the alpha, omega-diene; adding additional solvent and a post cure quenching agent to the gel; and subjecting the solvent, the post cure quenching agent, and the gel to shear force until a paste is formed.

2 Claims, No Drawings

QUENCHING POST CURE

CROSS-REFERENCE TO RELATED APPLICATIONS

This application is an improvement in methods generally described in a prior copending application U.S. Ser. No. 08/618,616, filed on Mar. 20, 1996, entitled "Silicone Oils and Solvents Thickened by Silicone Elastomers", now U.S. Pat. No. 5,654,362, which issued on Aug. 5, 1997. The prior application is assigned to the same assignee as this application. The prior application is considered incorporated herein by reference thereto, and will be referred to hereinafter as the '362 patent.

BACKGROUND OF THE INVENTION

This invention is directed to methods for the quenching of post cure occurring in the thickening of siloxanes with silicone elastomers.

In my '362 patent, silicone elastomers are used in the thickening of silicone fluids and organic solvents. These elastomers are formed by a hydrosilylation reaction between a multifunctional $\equiv$SiH siloxane and an $\alpha,\omega$-diene.

According to my '362 patent, one scheme representative of a process that can be used in making a silicone elastomer suitable in thickening a low viscosity fluid is shown below:

Step 1 - Gelation $\alpha,\omega$-diene+$\equiv$Si—H Siloxane+Fluid+Pt Catalyst→Gel Step 2 - Shear & Swell Gel+More Fluid→Paste When a network is formed in such a reaction, I have determined that steric hindrance of the crosslinked structure prevents the reaction from reaching completion. This is believed to be due to the fact that a small amount of residual functionality will remain even after long reaction times, and that unreacted functionalities will tend to meet each other when the gel is sheared and swollen. I have termed the phenomenon post cure. While residual reactivity will provide a smooth, pasty product, and a gel, in order to maintain a finer appearance and a more flowable rheology of the final paste, the post cure phenomena should be eliminated.

This can be achieved, according to my invention, by either deactivating the platinum (Pt) catalyst or by quenching any residual $\equiv$SiH functionality.

BRIEF SUMMARY OF THE INVENTION

I have discovered that the post cure caused by the residual crosslinking hydrosilylation reactions which typically occur in the preparation of silicone elastomers can be terminated by introducing either (i) a strong platinum complexing ligand, (ii) an $\equiv$SiH quencher such as a vinylsiloxane or a vinylsilane, or (iii) a terminal alkyne. In my method, and especially in the case of using a vinylsiloxane as the preferred quencher, the resulting material has been found not to be contaminated by any toxic ingredient. This is an important feature and advantage when the resulting product is intended for use in the personal care or the health care arena.

These and other features of my invention will become apparent from a consideration of the detailed description.

DETAILED DESCRIPTION OF THE INVENTION

As noted above, post cure caused by residual crosslinking hydrosilylation reactions occurring in silicone elastomers can be terminated by introducing (i) a strong platinum complexing ligand, (ii) an $\equiv$SiH quencher such as a vinylsiloxane or a vinylsilane, or (iii) a terminal alkyne.

A strong platinum coordinating ligand has been found to be effective in deactivating the functioning of the catalyst used in the preparation of silicone elastomers. Suitable ligands include phosphines, amines, and organic sulfides. Representative ligands useful herein are trialkyl and triaryl phosphines such as triphenylphosphine $PPh_3$; amines, diamines, and triamines such as n-butylamine $CH_3(CH_2)_3NH_2$, triethanolamine $(HOCH_2CH_2)_3N$, and tetramethylethylenediamine $(CH_3)_2NCH_2CH_2N(CH_3)_2$; and organic sulfides such as ethyl phenyl sulfide $C_6H_5SC_2H_5$.

I have determined that by adding one equivalent or more of a ligand at the shear & swell step in the process, any crosslinking reactions will be terminated, and therefore no post cure will occur. However, many strong ligands to platinum tend to be toxic, and so their presence even in small amounts may not be suitable in some applications, i.e., as in for example personal care and health care products. This may limit the application of this particular feature of my invention to industrial applications.

Residual $\equiv$SiH according to my invention can also be quenched by molecules containing unsaturation such as alkene and alkyne; OH, or any other functionality that will react with $\equiv$SiH. I have determined that because the internal crosslinking reaction is competing with the quenching reaction, the quenching reaction has to be carried out faster or in a more preferred mode than the crosslinking reaction. For example, using a large quantity of a quencher is one mode to increase the competition in favor of the quenching reaction, but this mode may not be economical nor desirable in some applications.

I have found that vinylsiloxanes and/or vinylsilanes can be used to completely terminate post cure. Vinylsiloxanes are preferred to react with $\equiv$SiH over other alkenylsiloxanes. In my process of making a silicone paste, a vinylsiloxane is introduced at the shear & swell step. When this is carried out according to my invention, on-going reactions of residual functionalities will be shifted to reactions between the incoming vinylsiloxane and the residual $\equiv$SiH, and the crosslinking reaction will be terminated.

Preferably, a monovinylsiloxane should be used because it is not capable of crosslinking. However, in the situation where moles of the quencher are in a large excess relative to $\equiv$SiH, multivinylsiloxanes such as divinylsiloxane and trivinylsiloxane are also suitable for purposes of my invention as well.

Representative of some organosilicon monomers and polymers which can be used as quenching agents according to my invention are silanes such as vinyl-t-butyldimethylsilane, vinyldiethylmethylsilane, vinylethyldimethylsilane, vinyltriethylsilane, vinyltrimethylsilane, divinyldimethylsilane, and divinyltetramethyldisilane; and siloxanes such as vinylpentamethyldisiloxane, 1,3-divinyltetramethyldisiloxane, a vinyltrisiloxane having the structure $(CH_3)_3SiOSi(CH=CH_2)$ $(CH_3)OSi(CH_3)_3$, 1,5-divinylhexamethyltrisiloxane, and a divinylsiloxane oligomer having an average structure $(CH_2=CH)Me_2SiO(Me_2SiO)_8SiMe_2(CH=CH_2)$.

A schematic representation of a process according to my invention is shown below in which a vinylsiloxane is depicted as competing with hexenyl groups as follows:

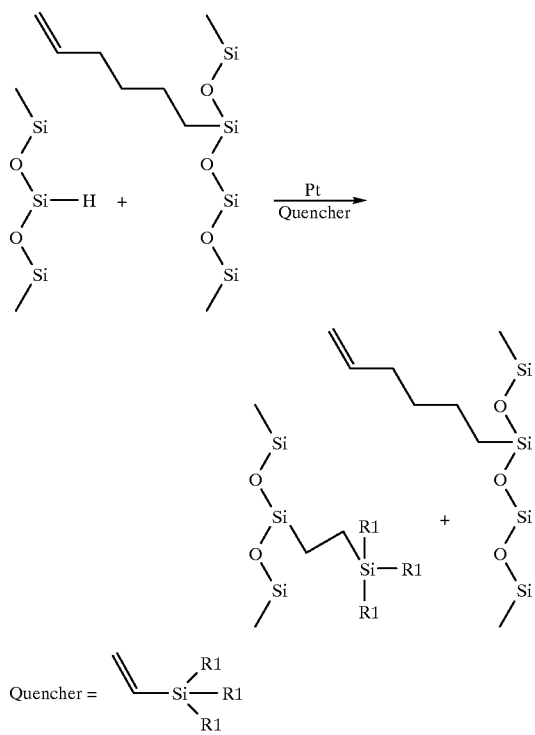

In another embodiment of my invention, post cure quenching can be achieved using a post cure quenching agent other than a ligand or a silicon containing monomer or polymer. In this alternate embodiment, an organic compound can be used such as a terminal alkyne.

I have determined that alkynes are more reactive than alkenes towards ≡Si—H in hydrosilylation reactions. Thus, when an alkyne is introduced at the shear & swell step, reactions of ≡Si—H to the alkenyl group will shift to an incoming alkyne. In this fashion, the crosslinking reaction will terminate.

Some examples of organic alkynes which can be used according to my invention are acetylene, propyne, 1-butyne, 1-pentyne, 4,4-dimethyl-1-pentyne, 1-hexyne, 5-methyl-1-hexyne, and 1-decyne.

It is also possible to use other unsaturated hydrocarbons such as alpha, omega-diynes of the formula $CH{\equiv}C(CH_2)_x C{\equiv}CH$; or alpha, omega-ene-ynes of the formula $CH_2{=}CH(CH_2)_x C{\equiv}CH$ where x is 1–20. Some representative examples of alpha, omega-diynes are 1,3-butadiyne $HC{\equiv}C—C{\equiv}CH$ and 1,5-hexadiyne (dipropargyl) $HC{\equiv}C—CH_2CH_2—C{\equiv}CH$. One example of a suitable alpha, omega-ene-yne is hexene-5-yne-1 $CH_2{=}CHCH_2CH_2C{\equiv}CH$.

Regardless of the type of post cure quenching agent selected to be used for the purposes herein, an excess of post cure quenching agent is required. This not only increases the competition, but more importantly, it ensures consumption of all of the residual ≡Si—H groups. In particular, when a multifunctional vinyl siloxane or an alkyne is employed, the quantity of post cure quenching agent to be employed should be calculated on a molar basis rather than on an equivalent basis.

The following examples are set forth in order to illustrate my invention in more detail.

Example 1 - Quenching with Vinyl trisiloxane

A gel is made using the following ingredients:

(i) an ≡SiH siloxane of the formula $Me_3SiO(Me_2SiO)_{93}(MeHSiO)_6SiMe_3$ which is an average structure 51 g
(ii) Decamethylcyclopentasiloxane (D5) 264.2 g
(iii) 1,5-hexadiene 1.82 g
(iv) Karstedt catalyst with a Pt content of 0.51% 0.058 g The above mixture was stirred in a capped container and heated at 55° C. before it gelled. The gel was heated in a 65°–70° C. oven for three hours. The gel was sheared and swollen with additional D5 to a silicone paste containing 10.2% of the elastomer. Vinyltrisiloxane $(CH_3)_3SiOSi(CH{=}CH_2)(CH_3)OSi(CH_3)_3$ in an amount of 200 mg was added and mixed with 91 g of the paste. The resulting product remained pasty for an indefinite length of time.

Karstedt's catalyst is a preferred platinum catalyst, and is described in Karstedt's U.S. Pat. Nos. 3,715,334 and 3,814,730, which are incorporated herein by reference. Karstedt's catalyst is a platinum divinyl tetramethyl disiloxane complex, typically containing about 0.5–1.0 weight percent of platinum, carried in a solvent such as toluene.

Example 2 - Comparative Example

The gel prepared in Example 1 was sheared and swollen to a silicone paste containing 10.2% of the elastomer in D5, and the paste was kept in a jar. No vinyltrisiloxane was added. The resulting paste gelled to a semisolid after 12 hours.

Example 3 - Quenching with Vinylsiloxane Oligomer

The same gel was made according to Example 1, and it was sheared and swollen to a silicone paste containing 10.2% of the elastomer in D5. A vinylsiloxane oligomer with the average structure $(CH_2{=}CH)Me_2SiO(Me_2SiO)_8SiMe_2(CH{=}CH_2)$ 260 mg was mixed with 114 g of the paste. No further gelation was observed and the product remained pasty.

Example 4 - Quenching with Terminal Alkyne

The same gel was made according to Example 1, and it was sheared and swollen to a silicone paste containing 10.2% of the elastomer in D5. 1-Decyne $CH_3(CH_2)_7C{\equiv}CH$ 120 mg was mixed with 100 g of the paste. No further gelation was observed and the product remained pasty.

Example 5 - Quenching with Ligand

The same gel was made according to Example 1, and it was sheared and swollen to a silicone paste containing 10.2% of the elastomer in D5. A triphenylphosphine $(C_6H_5)_3P$ solution containing 0.5 weight percent triphenylphosphine in ethyl acetate 150 mg, was mixed with 100 g of the paste. No further gelation was observed and the product remained pasty.

My invention is useful in any method involving silicone elastomers prepared by a crosslinking reaction between (A) ≡Si—H containing polysiloxanes and (B) an alpha, omega-diene, in the presence of a platinum catalyst and (C) a low molecular weight linear or cyclic polysiloxane. Such elastomers can be swollen with the low molecular weight polysiloxane under a shear force.

Typically, the ≡Si—H containing polysiloxane (A) is a polymer represented by the formula $R_3SiO(R'_2SiO)_a(R''HSiO)_bSiR_3$ designated herein as type $A^1$ and polymers of the formula $HR_2SiO(R'_2SiO)_cSiR_2H$ or formula $HR_2SiO(R'_2SiO)_a(R''HSiO)_bSiR_2H$ designated herein as type $A^2$. In these formulas, R, R', and R", are alkyl groups with 1–6 carbon atoms; a is 0–250; b is 1–250; and c is 0–250. The molar ratio of compounds $A^2:A^1$ is 0–20, preferably 0–5. In most preferred embodiments, compounds of types $A^1$ and $A^2$ are used in the reaction, however, it is possible to successfully conduct the reaction using only compounds of type $A^1$.

The alpha, omega-diene (B) is typically a compound of the formula $CH_2=CH(CH_2)_xCH=CH_2$ where x is 1–20. Representative alpha, omega-dienes are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

These addition and crosslinking reactions require a catalyst to effect reaction between the ≡-SiH containing polysiloxane and the alpha, omega-diene. Suitable catalysts are Group VIII transition metals, i.e., the noble metals. Such noble metal catalysts are described in U.S. Pat. No. 3,923,705, incorporated herein by reference to show platinum catalysts. A preferred platinum catalyst is Karstedt's catalyst described above.

Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are typically used in amounts from 0.00001–0.5 parts per 100 weight parts of the ≡SiH containing polysiloxane, preferably 0.00001–0.02 parts, most preferably 0.00001–0.002 parts.

The phrase low molecular weight silicone oil (C) is intended to include (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS).

VMS compounds correspond to the average unit formula $(CH_3)_aSiO_{(4-a)/2}$ in which a has an average value of two to three. The compounds contain siloxane units joined by ≡Si—O—Si≡ bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH_3)_3SiO\{(CH_3)_2SiO\}_ySi(CH_3)_3$. The value of y is 0–5. Cyclic VMS have the formula $\{(CH_3)_2SiO\}_z$. The value of z is 3–6. Preferably, these volatile methyl siloxane have boiling points less than about 250° C. and viscosities of about 0.65–5.0 centistoke ($mm^2$/s).

Representative linear volatile methyl siloxanes are hexamethyldisiloxane (MM) with a boiling point of 100° C., viscosity of 0.65 $mm^2$/s, and formula $Me_3SiOSiMe_3$; octamethyltrisiloxane (MDM) with a boiling point of 152° C., viscosity of 1.04 $mm^2$/s, and formula $Me_3SiOMe_2SiOSiMe_3$; decamethyltetrasiloxane ($MD_2M$) with a boiling point of 194° C., viscosity of 1.53 $mm^2$/s, and formula $Me_3SiO(Me_2SiO)_2SiMe_3$; dodecamethylpentasiloxane ($MD_3M$) with a boiling point of 229° C., viscosity of 2.06 $mm^2$/s, and formula $Me_3SiO(Me_2SiO)_3SiMe_3$; tetradecamethylhexasiloxane ($MD_4M$) with a boiling point of 245° C., viscosity of 2.63 $mm^2$/s, and formula $Me_3SiO(Me_2SiO)_4SiMe_3$; and hexadecamethylheptasiloxane ($MD_5M$) with a boiling point of 270° C., viscosity of 3.24 $mm^2$/s, and formula $Me_3SiO(Me_2SiO)_5SiMe_3$.

Representative cyclic volatile methyl siloxanes are hexamethylcyclotrisiloxane ($D_3$) a solid with a boiling point of 134° C. and formula $\{(Me_2)SiO\}_3$; octamethylcyclotetrasiloxane ($D_4$) with a boiling point of 176° C., viscosity of 2.3 $mm^2$/s, and formula $\{(Me_2)SiO\}_4$; decamethylcyclopentasiloxane ($D_5$) with a boiling point of 210° C., viscosity of 3.87 $mm^2$/s, and formula $\{(Me_2)SiO\}_5$; and dodecamethylcyclohexasiloxane ($D_6$) with a boiling point of 245° C., viscosity of 6.62 $mm^2$/s, and formula $\{(Me_2)SiO\}_6$.

Representative branched volatile methyl siloxanes and are heptamethyl-3-{(trimethylsilyl)oxy}trisiloxane ($M_3T$) with a boiling point of 192° C., viscosity of 1.57 $mm^2$/s, and formula $C_{10}H_{30}O_3Si_4$; hexamethyl-3,3,bis {(trimethylsilyl)oxy} trisiloxane ($M_4Q$) with a boiling point of 222° C., viscosity of 2.86 $mm^2$/s, and formula $C_{12}H_{36}O_4Si_5$; and pentamethyl {(trimethylsilyl)oxy} cyclotrisiloxane (MD3) with the formula $C_8H_{24} O_4Si_4$.

My process can include the use of low molecular weight linear and cyclic volatile and non-volatile alkyl and aryl siloxanes. Representative linear polysiloxanes are compounds of the formula $R_3SiO(R_2SiO)_ySiR_3$, and representative cyclic polysiloxanes are compounds of the formula $(R_2SiO)_z$. R is an alkyl group of 1–6 carbon atoms, or an aryl group such as phenyl. The value of y is 0–80, preferably 0–20. The value of z is 0–9, preferably 4–6. These polysiloxanes have viscosities generally in the range of about 1–100 centistoke ($mm^2$/s).

Other representative low molecular weight non-volatile polysiloxanes have the general structure:

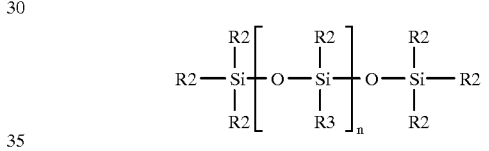

where n has a value to provide polymers with a viscosity in the range of about 100–1,000 centistoke ($mm^2$/sec).

R2 and R3 are alkyl radicals of 1–20 carbon atoms, or an aryl group such as phenyl. Typically, the value of n is about 80–375. Illustrative polysiloxanes are polydimethylsiloxane, polydiethylsiloxane, polymethylethylsiloxane, polymethylphenylsiloxane, and polydiphenylsiloxane.

Low molecular weight functional polysiloxanes can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

My invention is not limited to swelling silicone elastomers with only low molecular weight polysiloxanes. Other types of solvents can swell the silicone elastomer. Thus, a single solvent or a mixture of solvents may be used.

By solvent I mean (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Makers and Painters (VM&P) naphtha, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

I further intend to encompass by the term solvent, volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, I intend the term solvent to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Carrying out of the basic process over which my invention is an improvement, i.e., the basic process being the one generally represented by the '362 patent, is a matter of combining the $\equiv$SiH containing polysiloxane(s), the alpha, omega-diene, the low molecular weight silicone oil or other solvent, and the catalyst; and mixing these ingredients at room temperature until a gel is formed.

Additional amounts of the low molecular weight silicone oil or solvent are then added to the gel, and the resulting mixture is subjected to shear force to form the paste. Any type of mixing and shearing equipment may be used to perform these steps such as a batch mixer, planetary mixer, single or multiple screw extruder, dynamic or static mixer, colloid mill, homogenizer, sonolator, or a combination thereof.

Typically, that basic process uses approximately a 1:1 molar ratio of $\equiv$Si—H containing polysiloxane and alpha, omega-diene. Useful materials may also be prepared by carrying out the basic process with an excess of either the $\equiv$Si—H containing polysiloxane or the alpha, omega-diene, but this is a less efficient use of the materials. The remainder of the composition comprises the low molecular weight silicone oil or other solvent in amounts generally within the range of about 65–98 percent by weight of the composition, preferably about 80–98 percent by weight.

As noted above, my improvement resides in the feature of adding to the basic process a post cure quenching agent, at or during the shear & swell step in the basic process.

The silicone elastomer, silicone gel, and silicone paste compositions of my invention have particular value in the personal care arena. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they will function as leveling and spreading agents for pigments in make-ups, color cosmetics, foundations, blushes, lipsticks, lip balms, eyeliners, mascaras, oil removers, color cosmetic removers, and powders. They are useful as delivery systems for oil and water soluble substances such as vitamins. When incorporated into sticks, gels, lotions, aerosols, and roll-ons, the compositions impart a dry, silky-smooth, payout.

In addition, the compositions exhibit a variety of advantageous and beneficial properties such as clarity, shelf stability, and ease of preparation. Hence, they have wide application, but especially in antiperspirants, deodorants, in perfumes as a carrier, and for conditioning hair.

My silicone elastomers, gels, and pastes have uses beyond the personal care arena, including their use as a filler or insulation material for electrical cable, a soil or water barrier for in-ground stabilization, or as a replacement for epoxy materials used in coil-on-plug designs in the electronics industry. In these types of applications, a ligand may well be useable as a post cure quenching agent.

They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying Theological, physical, or energy absorbing properties of such phases in either their neat or finished condition. Again, in such applications, a ligand may be a viable alternative as post cure quenching agent.

In addition, my silicone elastomers, gels, and pastes are capable of functioning as carriers for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid.

Other variations may be made in monomers, polymers, copolymers, compounds, compositions, and methods described herein without departing from the essential features of my invention. The forms of my invention are exemplary only and not intended as limitations on their scope as defined in the appended claims.

I claim:

1. A method of thickening solvents comprising reacting (A) an $\equiv$Si—H containing polysiloxane of formula $R_3SiO(R'_2SiO)_a(R''HSiO)_bSiR_3$ and optionally an $\equiv$Si—H containing polysiloxane of formula $HR_2SiO(R'_2SiO)_cSiR_2H$ or formula $HR_2SiO(R'_2SiO)_a(R''HSiO)_bSiR_2H$ where R, R', and R'' are alkyl groups of 1–6 carbon atoms; a is 0–250; b is 1–250; and c is 0–250; with (B) an alpha, omega-diene of formula $CH_2=CH(CH_2)_xCH=CH_2$ where x is 1–20; conducting the reaction in the presence of a platinum catalyst and (C) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; continuing the reaction until a gel is formed by crosslinking and addition of $\equiv$Si—H across double bonds in the alpha, omega-diene; adding additional solvent and a post cure quenching agent to the gel; and subjecting the solvent, the post cure quenching agent, and the gel to shear force until a paste is formed; the post cure quenching agent being selected from the group consisting of vinyl-t-butyldimethylsilane, vinyldiethylmethylsilane, vinylethyldimethylsilane, vinyltriethylsilane, vinyltrimethylsilane, divinyldimethylsilane, divinyltetramethyldisilane, vinylpentamethyldisiloxane, 1,3-divinyltetramethyldisiloxane, vinyltrisiloxane $(CH_3)_3SiOSi(CH=CH_2)(CH_3)OSi(CH_3)_3$, 1,5-divinylhexamethyltrisiloxane, and divinylsiloxane oligomer $(CH_2=CH)Me_2SiO(Me_2SiO)_8SiMe_2(CH=CH_2)$.

2. A paste prepared according to the method in claim 1.

* * * * *